(12) United States Patent
Field

(10) Patent No.: US 12,115,311 B2
(45) Date of Patent: Oct. 15, 2024

(54) TRACHEAL TUBE AND METHOD OF ASSEMBLING A TRACHEOSTOMY TUBE

(71) Applicant: SMITHS MEDICAL INTERNATIONAL LIMITED, Ashford (GB)

(72) Inventor: Stephen James Field, Canterbury (GB)

(73) Assignee: Smiths Medical International Limited, Ashford (GB)

( * ) Notice: Subject to any disclaimer, the term of this patent is extended or adjusted under 35 U.S.C. 154(b) by 822 days.

(21) Appl. No.: 17/260,635

(22) PCT Filed: Jul. 9, 2019

(86) PCT No.: PCT/GB2019/000099
§ 371 (c)(1),
(2) Date: Jan. 15, 2021

(87) PCT Pub. No.: WO2020/025913
PCT Pub. Date: Feb. 6, 2020

(65) Prior Publication Data
US 2021/0275765 A1    Sep. 9, 2021

(30) Foreign Application Priority Data
Jul. 28, 2018   (GB) ..................................... 1812442

(51) Int. Cl.
*A61M 16/04*   (2006.01)
(52) U.S. Cl.
CPC ..... *A61M 16/0465* (2013.01); *A61M 2207/00* (2013.01); *A61M 2240/00* (2013.01)
(58) Field of Classification Search
CPC .. A61M 16/00; A61M 16/04; A61M 16/0402; A61M 16/0463; A61M 16/0465;
(Continued)

(56) References Cited

U.S. PATENT DOCUMENTS 3,388,705 A    6/1968   Grosshandler
3,824,999 A    7/1974   King
(Continued)

FOREIGN PATENT DOCUMENTS

GB    649230 A      1/1951
WO    03018095 A1   3/2003
(Continued)

OTHER PUBLICATIONS

PCT International Search Report for PCT/GB2019/000099 Form 210 dated Oct. 28, 2019.

(Continued)

*Primary Examiner* — Colin W Stuart
(74) *Attorney, Agent, or Firm* — Louis Woo

(57) ABSTRACT

A paediatric tracheostomy tube is provided in two parts. One part is a patient end portion (13) having a silicone shaft (10) arranged to locate in the trachea. The machine end is formed with a mounting flange (20) adapted to lie against the neck and has a low profile coupling (21) on its machine side. The other part is a machine end portion (23) having a flexible, corrugated shaft (10') of polypropylene with a low profile coupling (26) at its patient end adapted to engage the coupling (21) on the flange as a twist fit. The machine end of the machine end portion (23) has a tapered male coupling (25) adapted to fit with a female coupling on a breathing tube, the male coupling having a larger profile than the coupling (26) on the patient end of the machine end portion (23) and the coupling (21) on the flange.

10 Claims, 1 Drawing Sheet

(58) Field of Classification Search
CPC .......... A61M 16/0475; A61M 16/0488; A61M 16/0497; A61M 2207/00; A61M 2240/00
See application file for complete search history.

(56) References Cited

U.S. PATENT DOCUMENTS

| | | | |
|---|---|---|---|
| 4,516,573 | A | 5/1985 | Gedeon |
| 4,805,611 | A | 2/1989 | Hodgkins |
| 6,398,266 | B1 | 6/2002 | Crump |
| 2004/0069307 | A1 | 4/2004 | Rich |
| 2007/0181131 | A1 | 8/2007 | Lowery |
| 2009/0139529 | A1 | 6/2009 | Worley |
| 2011/0067699 | A1 | 3/2011 | Caruso |
| 2011/0139151 | A1 | 6/2011 | Burns |
| 2012/0006330 | A1 | 1/2012 | Barbot |
| 2012/0017905 | A1 | 1/2012 | Sata |
| 2014/0102459 | A1 | 4/2014 | Vilsi |
| 2015/0297851 | A1* | 10/2015 | Smith ............... A61M 16/0468 128/203.14 |
| 2018/0093056 | A1* | 4/2018 | Hingley ............ A61M 16/0402 |
| 2018/0093061 | A1 | 4/2018 | Fuller |
| 2018/0207381 | A1* | 7/2018 | Winthrop .......... A61M 16/0497 |
| 2018/0353719 | A1* | 12/2018 | Dexter ................ A61M 16/049 |

FOREIGN PATENT DOCUMENTS

| | | |
|---|---|---|
| WO | 2011020985 A1 | 2/2011 |
| WO | 2015113338 A1 | 8/2015 |

OTHER PUBLICATIONS

PCT Written Opinion of the International Searching Authority Form 237.

* cited by examiner

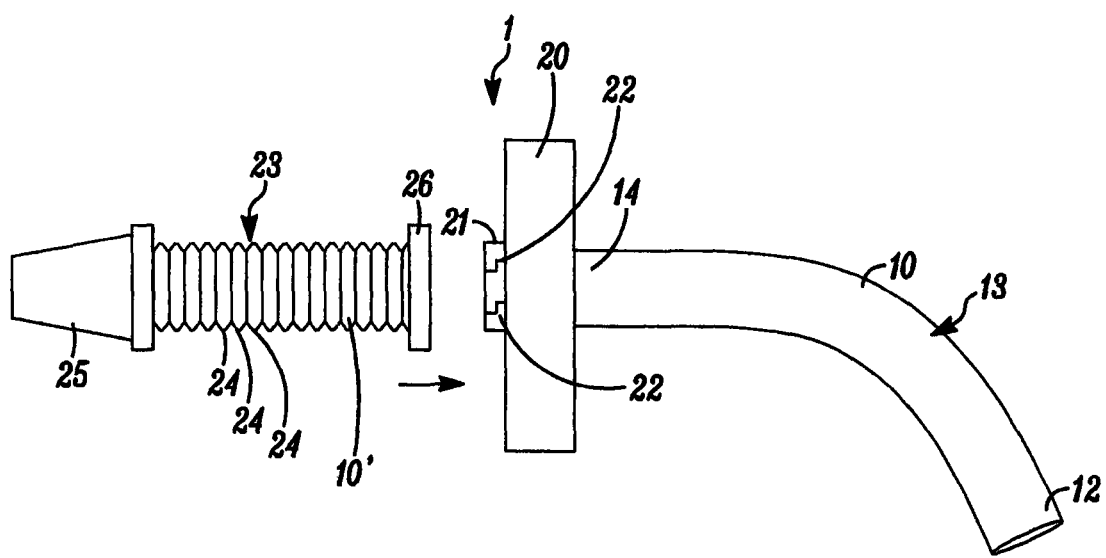

TRACHEAL TUBE AND METHOD OF ASSEMBLING A TRACHEOSTOMY TUBE

This invention relates to tracheal tubes of the kind having a shaft with a patient end portion adapted to extend into the body forwardly of a mounting flange and a machine end portion adapted to project rearwardly of the flange away from the patient.

Tracheal tubes are used to enable ventilation, respiration or spontaneous breathing of a patient. Endotracheal tubes are inserted via the mouth or nose so that one end locates in the trachea and the other end locates outside the patient. Tracheostomy tubes are inserted into the trachea via a surgically-formed opening in the neck. Tracheostomy tubes can be inserted by different techniques, such as the surgical cut-down procedure carried out in an operating theatre or a cricothyroidotomy procedure, which may be carried out in emergency situations.

Tracheostomy tubes are generally used for more long-term ventilation or where it is not possible to insert an airway through the mouth or nose. The patient is often conscious while breathing through a tracheostomy tube, which may be open to atmosphere or connected by tubing to some form of ventilator. The tube is secured in position by means of a flange fixed with the machine end of the tube and positioned to extend outwardly on opposite sides of the tube.

Tracheostomy tubes can be made of various materials and are usually of a bendable plastics material such as PVC, polyurethane or silicone. Silicone tubes are particularly advantageous for long-term use because they can be highly flexible, making them less traumatic and damaging to tissue contacted by the tube. The silicone material is also highly compatible with patient tissue with a very low risk of granulation. Another advantage of silicone is that it is resistant to high temperatures, which enables it to be repeatedly autoclaved and reused. The soft nature of silicone tubes, however, means that they can be easily kinked and occluded by external pressure unless measures are taken to avoid this. Often, silicone tubes are reinforced by means of a stiff helical member extending along the tube, either along substantially their entire length or along only a part of the length. Typically, the reinforcement member is a metal wire. Although metal wire reinforcements are ideal to give the degree of kink and crush resistance desired they have the disadvantage of not being entirely compatible with MRI (magnetic resonance imaging) equipment or being only MRI conditional.

It has been proposed to use reinforcements made of non-ferromagnetic metals but there is reluctance to use even these materials, especially with higher resolution MRI equipment with field strengths of between 6T and 10T. MRI conditional materials may not cause a danger to the patient but they can distort the magnetic field leading to image artefacts.

It has also been proposed to use stiffer plastics filaments, such as of nylon or aramid, as the helical reinforcement of silicone tubes. These can provide some degree of reinforcement although not as much as metals. These plastics have a further disadvantage that they are often not as heat resistant as silicone so they can be prone to damage by the high temperatures met during autoclave treatment.

It is known for tracheal tubes to have a machine end portion of the shaft extending outwardly beyond the point where the tube enters the body. A silicone paediatric tracheostomy tube sold by Smiths Medical under the Bivona® FlexTend™ trade mark (Bivona is a Registered Trade Mark of Smiths Medical) has such a machine end portion extending outwardly beyond the supporting flange. This tube is reinforced with a helical metal wire and is terminated by a connector by which connection is made to the tube. Because the machine end portion extends freely outside the body and is connected to breathing tubing it would be particularly prone to kinking if not reinforced.

It is an object of the present invention to provide an alternative tracheal tube.

According to one aspect of the present invention there is provided a tracheal tube of the above-specified kind, characterised in that the machine end portion is formed separately of the patient end portion and has a shaft provided at its machine end with a male tapered coupling adapted for mating connection with a female tapered coupling, that the machine side of the mounting flange and the patient end of the machine end portion are provided with engaging couplings of a lower profile than the mating coupling at the machine end of the machine end portion, and that the shaft of the machine end portion has its multiple recesses in its external surface arranged to increase the flexibility of the shaft of the machine end portion.

The recesses are preferably provided by a series of corrugations along the machine end portion. The corrugations are preferably formed on both the external and internal surface of the shaft of the machine end portion. The engaging couplings on the mounting flange and on the patient end of the machine end portion are provided by teeth that engage one another when one part is twisted relative to the other. The patient end portion of the tube is preferably of a silicone material. The shaft of the machine end portion is preferably of polypropylene. The tube is preferably a tracheostomy tube and may be a paediatric tube.

According to another aspect of the present invention there is provided a method of assembling a tracheostomy tube including the steps of: providing a patient end portion with a mounting flange and a shaft adapted to extend into the body forwardly of a mounting flange, the machine side of the mounting flange being provided with a low profile coupling; providing a machine end portion having a shaft with a male tapered coupling at its machine end adapted for mating connection with a female tapered coupling, the shaft of the machine end portion being formed with recesses on its external surface arranged to increase the flexibility of the shaft, the patient end of the machine end portion being provided with a low profile coupling, the couplings on the mounting flange and at the patient end of the machine end portion having a lower profile than the male tapered coupling at the machine end of the machine end portion; and removably fitting the coupling at the patient end of the machine end portion to the coupling on the mounting flange to join the machine end portion with the patient end portion.

According to a further aspect of the present invention there is provided a tracheostomy tube made by a method according to the above other aspect of the present invention.

A paediatric tracheostomy tube according to the present invention will now be described, by way of example, with reference to the accompanying drawing, wherein:

FIG. 1 is a side elevation view of the tracheostomy tube showing its parts separated before assembly.

The tracheostomy tube 1 has a curved shaft 10 of circular section along a forward, patient end portion 13 formed from a flexible silicone material having a durometer (Shore A) between 60 and 70. The dimensions of the tube are selected to be suitable for use in paediatric or neonatal patients. The shaft 10 has a patient end 12 adapted to be located within the trachea of the patient. The tube 1 is shown without a sealing cuff but a conventional sealing cuff could be attached towards its patient end.

The machine end 14 of the forward, patient end portion 13 of the shaft 10 is adapted, during use, to be located externally of the tracheostomy opening formed in the patient's neck. The machine end 14 of the forward portion 13 of the shaft 10 is bonded or integrally formed with a radially-extending support flange 20 adapted to lie against the skin surface of the neck on either side of the tracheostomy stoma. The flange 20 is located about midway along the total length of the shaft 10. The flange 20 has openings (not shown) at opposite ends for attachment to a neck strap (not shown) used to support the tube 1 with the patient's neck. The rear, machine side of the flange 20 has an integrally moulded low-profile locking ring 21 around the opening of the bore of the shaft 10. The locking ring 21 is formed around its outer, circumference with a number of locking teeth 22. Other locking mechanisms are possible and the locking ring could be formed separately and subsequently attached to the flange.

The shaft 10 also includes a machine end portion 23 extending rearwardly in a machine direction away from the flange 20 and forming a rear part 10' of the shaft. The machine end portion 23 is moulded separately from the flange 20 and forward portion 13 and is of a material that is different from and stiffer than that of the flange and forward portion of the shaft. Typically the machine end portion 23 of the shaft 10 may be moulded or extruded of polypropylene or a similar material. The machine end portion 23 of the shaft 10 is formed with a series of recesses formed by multiple annular corrugations 24 along its length and is integrally moulded with a conventional 15 mm male tapered coupling 25 at its rear, machine end. The corrugations 24 are preferably formed on both the outer and inner surface of the machine end portion 23 but could just be formed on one surface. The material of the machine end portion 23 need not be stiffer than that of the patient end portion 10. The flexibility of the machine end portion could be increased by recesses in ways other than by corrugations such as by multiple discrete cavities spaced over the surface.

At its opposite, patient end the machine end portion 23 is moulded with a low-profile locking ring 26 with an inner diameter equal to the outer diameter of the locking ring 21 on the flange 20. The inner surface of the locking ring 26 on the machine end portion 23 is formed with teeth (not shown) adapted to engage with the teeth 22 on the outside of the locking ring 21 on the flange 20. The teeth 22 on the locking ring 21 on the flange 20 and the teeth on the locking ring 26 on the machine end portion 23 are shaped so that they engage each other when the machine side locking ring 26 is positioned over the patient side locking ring 21 and is twisted through about 90° relative to the flange. The thickness of the locking ring 26 on the machine end portion 23 is approximately equal to the thickness of the locking ring 21 on the flange 20 so that, when engaged and locked with one another the combined length or thickness of the two locking rings does not exceed that of the thicker or longer of the two rings.

When the machine end portion 23 is locked onto the flange 20 it forms a part of the tracheostomy tube 1. Ventilation connection is made to the tube 1 by connecting a conventional 22 mm breathing circuit terminated by a conventional 15 mm, 8 mm or other female coupling (not shown) to the male coupling 25 on the tube 1. The length and flexible nature of the machine end portion 23 helps isolate the breathing circuit from the patient end portion 13 of the tube 1, thereby avoiding the encumbrance of the relatively large diameter breathing circuit close to a very small patient. It also helps reduce the forces applied to the patient end portion 13 of the shaft 10 from the mass and leverage of the breathing circuit, thereby reducing trauma to patient tissue.

Because the machine end portion 23 can be unlocked from the flange 20 this can be disposed of when it becomes soiled and replaced by a new machine end portion locked in position on the flange. By making the machine end portion 23 from a relatively stiff material and rendering it flexible by corrugations this portion can be highly flexible with a low risk of kinking and buckling but without the need to compromise the flexibility of the portion 13 within the patient. It also avoids the need to use metal reinforcing elements so that the entire tube can be used safely in MRI environments and without any image distortion.

Because the machine end portion is separable from the patient end portion there is no need for any metal or non-metal reinforcement in the patient end portion of the tube. This enables the patient end part of the tube to be autoclaved after use and then reused. In this way the cost of maintaining a patient with a tracheostomy tube can be reduced and the cost and environmental damage caused by disposal of clinical waste can also be reduced.

It will be appreciated that the tube could be of different sizes or shapes according to the application.

The invention is particularly advantageous in paediatric size tubes because the small diameter shafts in such tubes makes them more prone to kinking but is not confined to paediatric sizes.

The invention claimed is:

1. A tracheal tube having a shaft with a patient end portion adapted to extend into a body forwardly of a mounting flange and a machine end portion adapted to project rearwardly of the flange away from a patient, characterised in that the machine end portion is formed separately of the patient end portion and has a shaft provided at its machine end with a male mating coupling adapted for mating connection with a female mating coupling, that a machine side of the mounting flange and a patient end of the machine end portion are provided with engaging couplings of a lower profile than the male mating coupling at the machine end of the machine end portion, and that the shaft of the machine end portion has multiple recesses in its external surface arranged to increase the flexibility of the shaft of the machine end portion, wherein the engaging couplings are locking ring couplings that engage to each other by twisting, and wherein the machine end portion is removable from the patient end portion.

2. A tracheal tube according to claim 1, characterised in that the recesses are provided by a series of corrugations along the machine end portion.

3. A tracheal tube according to claim 2, characterised in that the series of corrugations are formed on both the external and internal surface of the shaft of the machine end portion.

4. A tracheal tube according to claim 1, characterised in that the engaging couplings on the mounting flange and on the patient end of the machine end portion are provided by teeth that engage one another when one part is twisted relative to the other.

5. A tracheal tube according to claim 1, characterised in that the patient end portion of the tube is of a silicone material.

6. A tracheal tube according to claim 1, characterised in that the shaft of the machine end portion is of polypropylene.

7. A tracheal tube according to claim 1, wherein the tube is a tracheostomy tube.

8. A tracheal tube according to claim 1, wherein the tube is a pediatric tube.

9. A method of assembling a tracheostomy tube including the steps of: providing a patient end portion with a mounting flange and a shaft adapted to extend into a body forwardly of the mounting flange, a machine side of the mounting flange being provided with a low profile coupling; providing a machine end portion having a shaft with a male tapered coupling at its machine end adapted for mating connection with a female tapered coupling, the shaft of the machine end portion being formed with recesses on its external surface arranged to increase the flexibility of the shaft, a patient end of the machine end portion being provided with a low profile coupling, the couplings on the mounting flange and at the patient end of the machine end portion are locking ring couplings having a lower profile than the male tapered coupling at the machine end of the machine end portion and are adapted to engage to each other by twisting; and removably fitting the coupling at the patient end of the machine end portion to the coupling on the mounting flange to join the machine end portion with the patient end portion.

10. A method of making a tracheostomy tube having a patient end portion adapted to extend into a body of a patient forwardly of a mounting flange and a machine end portion formed with recesses on its external surface adapted to project rearwardly of the flange away from the patient, respective low profile twist locking couplings on a machine end of the flange and on a patient end of the machine end portion adapted to engage to each other, the locking couplings each having a lower profile than a male mating coupling at a machine end of the machine end portion, the machine end portion being removable from the patient end portion, wherein the tracheostomy tube is assembled by comprising the steps of:

providing a shaft including a body with the patient end portion forward of the mounting flange and the machine end portion rearwardly of the flange;

providing a machine side of the mounting flange with one of the low profile locking couplings;

providing the machine end portion with the male mating coupling at its machine end adapted for mating connection with a female mating coupling, forming the recess on the external surface of the machine end portion to increase the flexibility of the shaft, and providing the patient end of the machine end portion with the other of the low profile locking couplings configuring the low profile locking couplings on the mounting flange and at the patient end of the machine end portion as locking couplings adapted to engage to each other by twisting, and configuring the locking couplings to have a lower profile than the male mating coupling at the machine end of the machine end portion; and removably fitting the low profile locking coupling at the patient end of the machine end portion to the low profile locking coupling on the mounting flange to join the machine end portion with the patient end portion.

\* \* \* \* \*